United States Patent
Couvreur et al.

(10) Patent No.: US 7,704,972 B2
(45) Date of Patent: Apr. 27, 2010

(54) GEMCITABINE DERIVATIVES NANOPARTICLES

(75) Inventors: Patrick Couvreur, Villebon sur Yvette (FR); Barbara Stella, Torino (IT); Luigi Cattel, Piedmont-Torinese (IT); Flavio Rocco, Nichelino (IT); Jack-Michel Renoir, L'Hay les Roses (FR); Véronique Rosilio, Paris (FR)

(73) Assignees: Centre National de la Recherche Scientifique, Paris (FR); Universite Paris-SUD, Orsay (FR)

( * ) Notice: Subject to any disclaimer, the term of this patent is extended or adjusted under 35 U.S.C. 154(b) by 579 days.

(21) Appl. No.: 11/631,075

(22) PCT Filed: Jun. 23, 2005

(86) PCT No.: PCT/FR2005/050488

§ 371 (c)(1),
(2), (4) Date: Jun. 26, 2007

(87) PCT Pub. No.: WO2006/090029

PCT Pub. Date: Aug. 31, 2006

(65) Prior Publication Data

US 2009/0130214 A1     May 21, 2009

(30) Foreign Application Priority Data

Jun. 30, 2004   (FR) .................................. 04 51365

(51) Int. Cl.
*A01N 43/04* (2006.01)
*A61K 31/70* (2006.01)
(52) U.S. Cl. ........................... 514/49; 514/43; 536/28.1
(58) Field of Classification Search .................. None
See application file for complete search history.

(56) References Cited

U.S. PATENT DOCUMENTS

| 6,384,019 B1 * | 5/2002 | Myhren et al. ................. 514/49 |
| 6,524,595 B1 | 2/2003 | Perrier et al. |
| 2002/0042391 A1 | 4/2002 | Myhren et al. |

FOREIGN PATENT DOCUMENTS

| EP | 0693077 | 1/1996 |
| WO | 98/32762 | 7/1998 |

OTHER PUBLICATIONS

Kaul et al. Pharmaceutical Research (2002), vol. 19, pp. 1061-1067.*
Ceruti et al., Synthesis of (E)- and (Z)-29-methylidyne-2,3-oxidosqualene derivatives as inhibitors of liver and yeast oxidosqualene cyclase *J. Chem. Soc., Perkin Trans. 1*, 2002, 1477-1488.
Fessi et al., Nanocapsule formation by interfacial polymer deposition following solvent displacement *International Journal of Pharmaceutics*, 55 (1989) R1-R4.
Heinemann et al., Comparison of the Cellular Pharmacokinetics and Toxicity of 2',2'-Difluorodeoxycytidine and 1-β-D-Arabinofuranosylcytosine *Cancer Research* 48, 4024-4031, Jul. 15, 1988.
Heinemann et al., Cellular Elimination of 2',2'-Difluorodeoxycytidine 5'-Triphosphate: A Mechanism of Self-Potentiation *Cancer Research* 52, 533-539, Feb. 1, 1992.
Hertel et al., Evaluation of the Antitumor Activity of Gemcitabine (2',2'-Difluoro-2'-deoxycytidine) *Cancer Research* 50, 4417-4422, Jul. 15, 1990.
Plunkett, et al., Gemcitabine: Metabolism, Mechanisms of Action, and Self-Potentiation *Seminars in Oncology* vol. 22, No. 4 Suppl II (Aug.), 1995: pp. 3-10.
Sharma et al., Reversed-phase high-performance liquid chromatographic determination of taxol in mouse plasma *Journal of Chromatography* B, 655, (1994) 315-319.
Storniolo et al., Preclinical, Pharmacologic, and Phase I Studies of Gemcitabine *Seminars in Oncology* vol. 24, No. 2 Suppl 7 (Apr.), 1997: pp. S7-2-S7-7.
van Tamelen, Bioorganic Chemistry: Sterols and Acyclic Terpene Terminal Epoxides *Sterols and Acyclic Terpene Terminal Epoxides* Apr. 1968 111-120.

* cited by examiner

*Primary Examiner*—Patrick T Lewis
(74) *Attorney, Agent, or Firm*—Young & Thompson

(57) ABSTRACT

The invention concerns a 2',2'-difluoro-2'-deoxycytidine derivative of general formula (I), wherein: $R_1$, $R_2$ and $R_3$, identical or different, represent independently of one another, a hydrogen atom or an at least $C_{18}$ hydrocarbon acyl radical and of such conformation that it is capable of providing the compound of general formula (I), a compacted form in a polar solvent medium, at least one of groups $R_1$, $R_2$ and $R_3$ being other than a hydrogen atom.

19 Claims, 3 Drawing Sheets

GEMCITABINE DERIVATIVES NANOPARTICLES

The present invention proposes novel derivatives of 2',2'-difluoro-2'-deoxycytidine (gemcitabine) of particular interest for their aptitude to organize themselves into nanoparticles.

Gemcitabine is an anti-cancer agent analogous to deoxycytidine, which is active against cancerous tumors of the colon, lung, pancreas, breast, bladder, ovaries etc (Hertel L. W. et al, Cancer Res., 50; 1990, 4417-4422 and Plunkett W. et al, Anticancer Drugs, 6 (Suppl. 6); 1995, 7-13). Its chemical structure is similar to that of cytarabine (Ara-C) with the exception of the presence of two geminal fluorine atoms located in the 2'-position of the deoxyribose sugar. This structural difference has the advantageous effect of increasing the lipophilic nature and membrane permeation of the gemcitabine molecule compared with that of cytarabine, and thus increasing toxicity (Heinemann V. et al, Cancer Res., 48; 1988, 4024-4031).

The mechanism for the action of gemcitabine can be explained as follows.

Gemcitabine is activated on the intracellular level by phosphorylation in the 5'-position by the action of deoxycytidinekinase, and is thus transformed into its triphosphate derivative. This is then incorporated into the DNA chain on replication, resulting in terminating chain elongation and death of the cell (Plunkett W. et al, Semin. Oncol., 22 (4 Suppl. 11); 1995, 3-10).

However, gemcitabine is also metabolized by the action of deoxycytidine deaminase principally located in the blood, liver and kidney, into its uracile derivative which turns out to be completely inactive (Heinemann V. et al, Cancer Res., 52; 1992, 533-539). As a result, when gemcitabine is administered intravenously, it has a non optimum anti-cancer activity because of the significantly reduced plasma half-life (Storniolo A. M. et al, Semin. Oncol., 24 (2 Suppl. 7); 1997, S7-2-S7-7).

To protect gemcitabine against said deamination, a proposal has been made to covalently couple its amino radical in the 4-position with an acyclic chain. Such an alternative has been considered in particular in European patent EP-A-0 986 570, which describes esters and amides of gemcitabine in which the 3'- and/or 5'-OH groups and/or N4-amino group are derivatized with saturated or mono-unsaturated $C_{18}$ to $C_{20}$ chains. However, the increase in anti-cancer activity observed with such lipophilic derivatives compared with gemcitabine is in this case obtained to the detriment of their solubility in aqueous media. Because of their highly lipophilic nature, such derivatives turn out to be barely compatible with intravenous administration.

The precise objective of the present invention is to propose novel gemcitabine derivatives endowed with an anti-cancer activity which is superior to that of gemcitabine due to significant stability to metabolization and an extended plasma half-life which is nevertheless compatible with parenteral administration, in particular intravenous administration.

More precisely, in a first aspect the present invention concerns a 2',2'-difluoro-2'-deoxycytidine derivative with general formula (I):

in which:

$R_1$, $R_2$ and $R_3$, which may be identical or different, independently of each other represent a hydrogen atom or an at least $C_{18}$ hydrocarbon acyl radical with a conformation such that it is capable of endowing said compound with general formula (I) with a compacted form, in particular of the nanoparticulate type, in a polar solvent medium; at least one of groups $R_1$, $R_2$ and $R_3$ being other than a hydrogen atom.

In a further aspect, the present invention concerns nanoparticles of gemcitabine derivatives in accordance with the present invention.

In a further aspect, the present invention concerns a process for preparing said nanoparticles, characterized in that it comprises:

dissolving a gemcitabine derivative in accordance with the invention in at least one organic solvent in a concentration which is sufficient to obtain, when adding the resulting mixture to an aqueous phase with stirring, the instantaneous formation of nanoparticles of said derivative in suspension in said aqueous phase and, if appropriate, isolating said nanoparticles.

In a further aspect, the present invention also concerns the use of said derivatives and nanoparticles in preparing a pharmaceutical composition endowed with an anti-cancer or anti-viral activity.

Further, it concerns a pharmaceutical composition comprising, as an active material, at least one derivative in accordance with the present invention, in particular in the form of nanoparticles.

Finally, it also concerns the use of squalenic acid or a derivative thereof in formulating a polar active principle with a molecular weight of 100 Da or more, in particular more than 150 Da, more particularly more than 200 Da, and in particular a nucleoside or the like, in the form of nanoparticles. Said use involves coupling, in particular by covalent bonding, at least one molecule of squalenic acid or a derivative thereof with one molecule of the active principle under consideration.

Surprisingly, the inventors have shown that covalently coupling gemcitabine with at least one molecule of a hydrocarbon derivative containing at least 18 carbon atoms can, provided that said hydrocarbon derivative has a conformation which can organize itself into a compacted form in a polar solvent medium, produce gemcitabine-based nanoparticles.

The gemcitabine derivatives advantageously play several roles.

Because of their highly hydrophobic nature rendering them insoluble in water, they can spontaneously organize themselves into particles by nano-precipitation.

Because the particles are very small, they can be administered intravenously in the form of an aqueous suspension and are thus compatible with vascular micro circulation.

The C$_{18}$ hydrocarbon derivatives considered in the context of the invention are generally covalently bound at the 3'- and/or 5'-OH group and/or at the 4-amino group of the gemcitabine.

More particularly, the unsaturated, non-linear acyclic hydrocarbon derivatives resemble terpene derivatives such as squalene and its derivatives.

Advantageously, said hydrocarbon derivative is a carboxylic acid. In this case, the covalent bond is more particularly of the ester type in the case of 3'- or 5'-OH groups, and of the amide type in the case of the 4-amino group.

Clearly, the gemcitabine derivatives of the present invention may be derivatives comprising two derivatisations, or even three derivatisations, which may be identical or different.

In a particular variation of the invention, the derivatives of the invention have at least one acyl hydrocarbon derivative with the hydrocarbon at the 4-amino group. It is then denoted the radical R$_1$.

More particularly, the gemcitabine derivatives of the invention have general formula (IA):

in which R$_2$ and R$_3$ are as defined above and R'$_1$ represents a squalenoyl radical or a derivative thereof.

Figure 1:
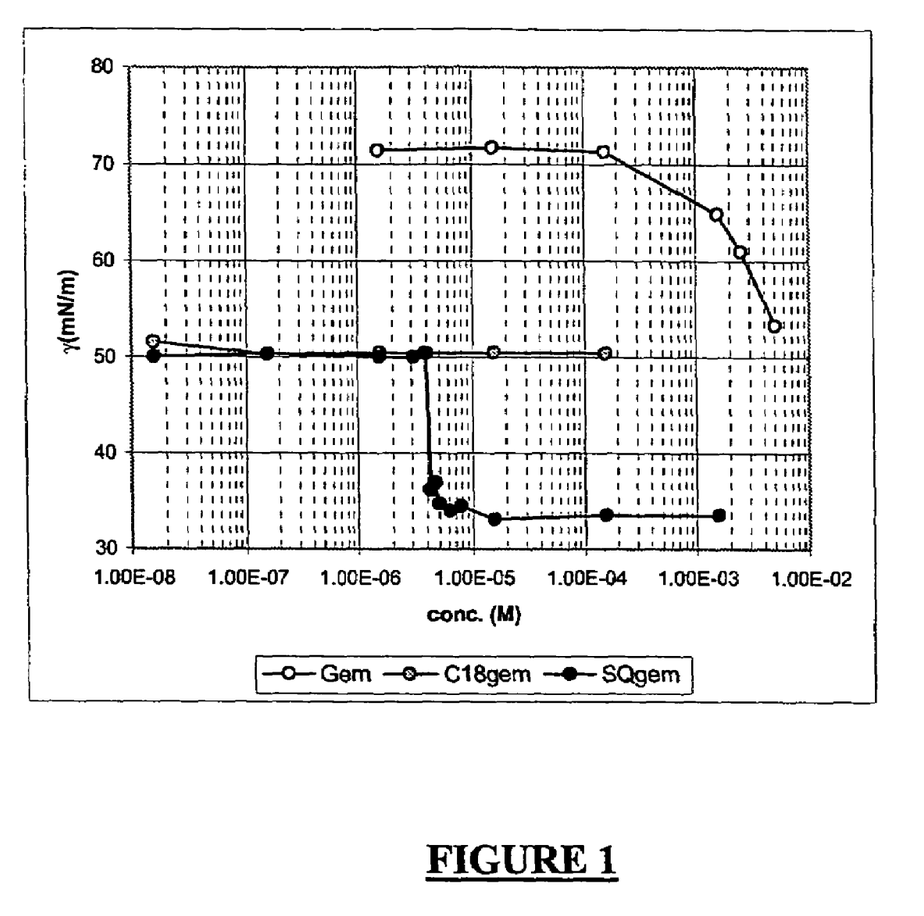
FIG. 1: This shows the change in surface tension ($\gamma$) of gemcitabine solutions (Gem), 4-(N)-stearoylgemcitabine (C18gem) and 4-(N)-squalenoylgemcitabine (SQgem) as a function of the concentration of solutions.
Figure 2:
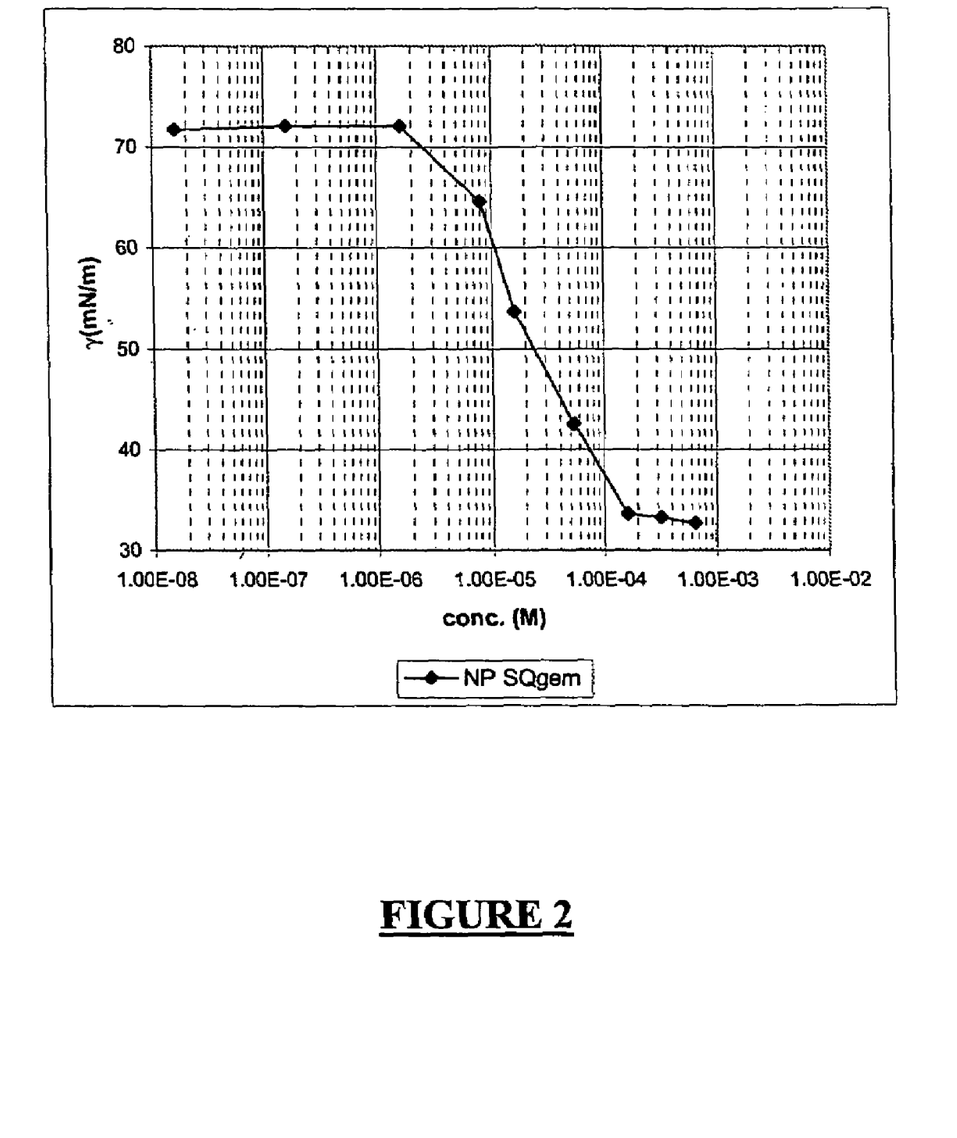
FIG. 2: This shows the change in surface tension (γ) of a suspension of SQgem nanoparticles (NP SQgem) as a function of concentration.

Within the context of the invention, the term "squalenoyl derivative" is intended to encompass substituted derivatives of the squalenoyl radical provided that the presence of the substituent or substituents does not have any significant effect on the original conformation of the radical. In other words, the radical must retain its ability to be compacted or to cause a significant reduction in the surface tension or a rapid drop in the surface tension when it is brought into the presence, starting from a certain concentration, of a polar solvent. This phenomenon is illustrated in FIGS. 1 and 2.

More particularly, R$_2$ and R$_3$ may then represent a hydrogen atom.

More particularly, the present invention concerns the 4-(N)-squalenoylgemcitabine derivative (SQgem).

Surprisingly, the inventors have determined that the derivatives of the present invention comprising a squalenoyl radical as the hydrocarbon radical have been shown to be particularly sensitive to the polarity of solvents, much like squalene. They then determined that bringing said gemcitabine derivatives into the presence of a polar solvent such as water, for example, results in the spontaneous formation of particles on a nanometric scale and are thus advantageously compatible with intravenous administration.

The gemcitabine derivative nanoparticles of the present invention can be accessed using conventional nano-precipitation techniques such as those described by Fessi H. et al., Int. J. Pharm., 55; 1989, R1-R4.

More precisely, the nanoparticles of the invention are obtained by dissolving a derivative in accordance with the present invention in an organic solvent such as acetone and/or ethanol. Adding the mixture obtained to an aqueous phase with stirring results in the instantaneous formation of the expected nanoparticles in the presence or absence of surfactant(s).

Advantageously, the process does not require the obligatory presence of surfactant(s) to obtain the nanoparticles of the invention. This property is particularly advantageous since a large number of segments are incompatible with in vivo application.

However, the use of surfactants, generally advantageously deprived of toxicity, may be envisaged in the present invention. That type of surfactant may provide access to even smaller sizes during the formation of the nanoparticles.

By way of non-limiting illustration of this type of surfactant which may be used in the present invention, the following may be cited: polyoxyethylene-polyoxypropylene copolymers, phospholipid derivatives and lipophilic derivatives of polyethylene glycol. A lipophilic derivative of polyethylene glycol which may be mentioned, for example, is polyethylene glycol cholesterol.

Examples of block polyoxyethylene-polyoxypropylene copolymers which may in particular be cited are polyoxyethylene-polyoxypropylene-polyoxyethylene triblock copolymers, also known as Poloxamers®, Pluronics® or Synperonics®, which are sold by BASF. Poloxamines® are closely related to these copolymer categories, and are constituted by hydrophobic segments (based on polyoxypropylene), hydrophilic segments (based on polyoxyethylene) and a central portion deriving from an ethylene diamine motif, which may also be employed.

The colloidal particle suspension may be stored as is, or evaporated to concentrate the nanoparticles of the invention.

In general, the mean size of the nanoparticles obtained is from 30 to 500 nm, in particular 50 to 250 nm, especially 70 to 200 nm or even 100 to 175 nm, measured by light diffusion using a Coulter® N4MD nanosizer, Coulter Electronics, Hialeah, USA.

This ability of the derivatives of the invention to result in the formation of nanoparticles is most probably the result of the specific behavior of these derivatives in an aqueous medium. As will become apparent from the following examples, a 4-(N)-squalenoylgemcitabine derivative turns out to behave very differently from gemcitabine or a 4-(N)-stearoylgemcitabine derivative in aqueous media. Only the derivative of the invention can significantly reduce the surface tension of water.

The inventors have also determined that it is possible to control the size of said particles through the quantity of gemcitabine derivative employed for nano-precipitation. Increasing the concentration of 4-(N)-squalenoylgemcitabine generally causes an increase in size, and vice versa, as will be seen in example 2 below. Further, and as mentioned above, this size may also be controlled by carrying out the formation of nanoparticles in the presence of surfactant(s).

The derivatives of the invention are also endowed with a much greater anti-tumoral activity than gemcitabine. Hence, the results shown below clearly show that 4-(N)-squalenoylgemcitabine nanoparticles turn out to be five to seven times more toxic than the gemcitabine molecule.

As indicated above, the compounds of the invention are thus advantageous for several reasons; firstly, the functionalization of gemcitabine in the 4-amino position effectively protects the amine function from the action of deoxycytidine deaminase, which is naturally responsible for the reduced plasma half-life of gemcitabine once administered intravenously.

However, said protection may also be increased in vivo because of the action of cellular enzymes, and result in the liberation of gemcitabine.

Further, conjugating gemcitabine with a hydrocarbon derivative in accordance with the invention, and more particularly with squalenic acid, endows the gemcitabine molecule with sufficient physico-chemical characteristics to endow it with an ability to form particles by nano-precipitation, with a particle size which proves to be compatible with parenteral administration and in particular intravenous administration.

The derivatives of the present invention may also be administered by all conventional pathways. However, as indicated above, said compositions are particularly advantageous when they are in the nanoparticulate form for parenteral administration.

Thus, in a further aspect, the invention concerns a pharmaceutical composition comprising at least, as an active material, a compound of the present invention especially in the form of nanoparticles. The derivatives of the present invention may be associated with at least one pharmaceutically acceptable vehicle.

Examples of pharmaceutical formulations which are compatible with the compositions of the invention which may be cited are:

intravenous injections or perfusions;
saline solutions or purified water;
compositions for inhalation;
compositions for ocular administration;
capsules, dragees and patches in particular incorporating water, calcium phosphate, sugars such as lactose, dextrose or mannitol, talc, stearic acid, starch, sodium bicarbonate and/or gelatin as vehicles.

When the compounds are used in dispersion in an aqueous solution, they may be associated with excipients of the sequestrating or chelating agent, anti-oxidant, pH modifying agents and/or buffer type.

The nanoparticles of the invention can clearly carry a multitude of reactive surface functions, such as hydroxyl functions or amines, for example. Thus, we can envisage binding all sorts of molecules to said functions, in particular by covalent bonds.

By way of non-limiting illustration of this type of molecule which may be associated with the nanoparticles, we can cite marker type molecules, compounds which can ensure a screening function, as well as any compound which can endow it with particular pharmacokinetic characteristics. Regarding this latter aspect, we can thus envisage binding lipophilic derivatives of polyethylene glycol to the surface of said nanoparticles, such as polyethylene glycol cholesterol or polyethylene glycol-phosphatidilethanolamine. A surface coating based on such a compound is advantageous as regards endowing increased vascular remanence to significantly reduce capture of nanoparticles by hepatic macrophages.

It is also possible to envisage non-covalent association of the compounds of the present invention and/or the corresponding nanoparticles with annex molecules as defined above. Said association may, for example, produce adsorption phenomena due to an affinity between the compounds of the invention and these other molecules.

As illustrated in example 4, polyethylene glycol in a conjugated form with cholesterol may be associated with a molecule of the present invention. Because of the natural affinity of squalene for cholesterol, the polyethylene glycol cholesterol conjugate associates with an active squalene-gemcitabine conjugate, and thus results in the formation of nanoparticles coated on the surface with polyethylene glycol. Further, and as mentioned above, the polyethylene glycol cholesterol conjugate advantageously, during the process of forming squalene-gemcitabine nanoparticles, acts like a surfactant because of its amphiphilic behaviour and thus stabilizes the colloidal solution, thereby reducing the size of the nanoparticles formed.

In addition to the compounds cited above, the pharmaceutical compositions of the invention may contain agents of the preservative, wetting, solubilising, staining and fragrancing type.

Clearly, the quantities of the derivatives of the invention which may be used, in particular for anti-cancer purposes can vary significantly depending on the mode of use and the mode of administration.

As an example, for systemic treatment intended for an adult patient, administering a derivative of the present invention in a dose of about 0.1 to 150 mg/kg of body weight per day, more particularly 1 to 40 mg/kg per day, may be envisaged.

In contrast, for topical administration, we can formulate at least one derivative of the present invention in an amount of 0.1% to 40% by weight or more with respect to the total weight of the pharmaceutical formulation under consideration.

It is also possible to co-administer at least one derivative of the present invention with at least one other active material which may also be beneficial with regards to the pathology under consideration.

Examples of said active materials which may be combined with the derivatives of the present invention which may be cited are other anti-cancer or cytostatic macromolecules or molecules (for example platinum salts, anthracyclines, mitotic spindle poisons, topoisomerase inhibitors, kinase inhibitors or metalloprotease inhibitors), corticoid (for example dexamethasone) or non-corticoid type anti-inflammatories or molecules with an immunoadjuvant activity (for example an antibody with anti-cancer activity). An association with hyperthermia, used in certain chemotherapies, may be envisaged. The derivatives of the present invention may also be combined with surgery and/or radiation therapy for the treatment of cancer.

In a further aspect, the invention concerns the use of squalenic acid or one of its derivatives to formulate an active principle with a polar nature with a molecular weight of 100 Da or more, in particular more than 150 Da, more particularly more than 200 Da, and in particular a nucleoside or the like as nanoparticles. The inventors have demonstrated that antiviral nucleosides which are covalently associated with a squalenic derivative could form nanoparticles. This aspect is illustrated in more detail in Examples 6, 7 and 8.

By way of non-limiting illustration of the antiviral nucleosides or the structural analogues which may be formulated in accordance with the invention, the following may be cited: didanosine, zidovidine and acyclovir, and also zalcitabine, gancyclovir, valacyclovir, la stavudine, lamivudine, abacavir, femtricitabine, famdoxovir, dOTC or sidophovir.

The following non-limiting examples and figures illustrate the field of the invention.

EXAMPLE 1

Preparation of 4-(N)-squalenoylgemcitabine (SQgem)

a) Synthesis of Squalenic Acid (SOCOOH)

1.16 ml of sulphuric acid was added to 11 ml of distilled water; next, 0.615 g (2.06 mmol) of $Na_2Cr_2O_7.2H_2O$ were carefully added to obtain chromic acid. 0.794 g (2.06 mmol) of squalenic aldehyde (SQCHO) (Ceruti M. et al, J. Chem. Soc, Perkin Trans, 1; 2002, 1477-1486) was dissolved in 16 ml of diethyl ether, stirring using a magnetic stirrer, and the flask was then cooled to 0° C. Next, the chromic acid was added dropwise to the SQCHO solution. The reaction was stirred with a magnetic stirrer at 0° C. for two hours. The crude product was purified by washing the organic phase with water and then by silica gel flash chromatography, eluting with petroleum ether/ether, 95:5. Yield: 35% (0.286 g, 0.714 mmol).

$^1$H NMR ($CD_3COCH_3$ 99.5% 300 MHz) δ: 5.11 (5H, m, CH vinyl), 2.38 (2H, t, $CH_2CH_2COOH$), 2.26 (2H, t, $CH_2CH_2COOH$), 2.13-1.86 (16H, m, $CH_2$ allyl), 1.65-1.59 (15H, m, $CH_3$ allyl), 1.26 (3H, s, $CH_3$ allyl). CIMS (isobutane) m/z 401 (100). EIMS m/z 400 (5), 357 (3), 331 (5), 289 (3), 208 (6), 136 (3), 81 (100).

b) Synthesis of 4-(V)-squalenoylsemcitabine 0.209 g (0.522 mmol) of SQCOOH obtained in a) dissolved in 1 ml of anhydrous tetrahydrofuran (THF) was placed in a three-necked flask provided with a flow meter and then 0.053 g (0.522 mmol) of triethylamine (TEA) dissolved in 0.5 ml of anhydrous THF were added, with stirring with a magnetic stirrer and with a stream of argon. The flask was then cooled to −15° C. 0.057 g (0.522 mmol) of ethylchloroformate dissolved in 2.15 ml of anhydrous THF was added dropwise to the reaction mixture. After 20 minutes at −15° C., 0.137 g (0.522 mmol) of gemcitabine dissolved in 2.72 ml of dimethylformamide (DMF) was added and the temperature was increased to +5° C. and finally to ambient temperature. The reaction was monitored by thin layer chromatography (dichloromethane/acetone, 50:50) and magnetic stirring was continued for several days until the amide had formed. The crude product was purified by silica gel flash chromatography eluting with dichloromethane/acetone 95:5 mixture. Yield: 55% (0.185 g, 0.287 mmol).

$^1$H NMR (pyridine-$d_5$ 99.5% 300 MHz) δ: 12.05 (1H, s, NHCO), 8.77 (1H, d, CH-6), 7.74 (1H, d, CH-5), 6.99 (1H, t, CH-1'), 5.30-5.02 (1H, m, CH-3' and 5H, m, CH vinyl), 4.47-4.31 (3H, m, CH-4' and $CH_2$-5'), 2.81 (2H, t, $NHCOCH_2$), 2.53 (2H, t, $NHCOCH_2CH_2$), 2.18-2.00 (16H, m, $CH_2$ allyl), 1.68-1.55 (18H, m, $CH_3$ allyl). CIMS (isobutane) m/z 646 (100). EIMS m/z 645 (10), 577 (8), 523 (7), 509 (18), 494 (10), 454 (15), 429 (24), 372 (100).

c) Preparation of Nanoparticles Constituted by 4-(N)-squalenoylsemcitabine

Particles constituted by SQgem were obtained using the nano-precipitation technique described by Fessi H. et al, Int. J. Pharm., 55; 1989, R1-R4. A sample of a 10 mg/ml solution of SQgem in ethanol was removed and added to acetone to the desired concentration to obtain a total of 2 ml of organic phase. This SQgem solution in the ethanol/acetone mixture was then added to 4 ml of MilliQ® water, with magnetic stirring. The particles formed instantaneously. After evaporating off the organic solvents under vacuum, a suspension of stable particles of SQgem was obtained. The suspension had to be stored at +4° C.

EXAMPLE 2

Physico-Chemical Characterization of Particles a) Determination of Size of Nanoparticles The size of the colloidal particles obtained in example 1 were monitored by quasi-elastic light diffusion using a nanosizer (Coulter® N4MD, Coulter Electronics, Hialeah, USA).

The colloidal suspensions were diluted in MilliQ® water so that the number of particles per ml was suitable for the measuring device.

The nanoparticle size was in the range 100 to 200 nm. It was monitored for the different concentrations of SQgem employed in the nano-precipitation process described in example 1. The results obtained are shown in Table I below.

TABLE I

| Concentration of SQgem in final suspension (mg/ml) | Mean hydrodynamic diameter (nm) | Standard deviation | Polydispersity index |
|---|---|---|---|
| 1 | 126.2 | 43.5 | 0.26 |
| 2 | 150.4 | 37.7 | 0.09 |
| 4 | 171.3 | 40.8 | 0.08 | b) Measurement of Surface Tension of Solutions of 4-(N)-squalenoylgemcitabine, and Stability Study The surface tension of an aqueous SQgem solution was measured at constant surface area at different concentrations using a Wilhemy blade tensometer and compared with that of a solution of gemcitabine (Gem) and 4-(N)-stearoylgemcitabine (C18gem) (Myhren F et al, Gemcitabine derivatives, U.S. patent no. 2002/0042391).

To prepare the various dilutions of SQgem and C18gem, it was necessary to start from an ethanolic solution; the percentage of ethanol in the final solution was 10% (the presence of ethanol reduces the surface tension of water from 72 mN/m to about 50 mN/m). The results are shown in FIG. 1.

It should be noted that SQgem reduces the surface tension at a concentration of $4 \times 10^{-6}$ M, which corresponds exactly to nanoparticle formation.

The stability of SQgem particles to dilution was also evaluated by measuring the surface tension at constant area of different dilutions of a suspension of SQgem particles. It is illustrated in FIG. 2.

EXAMPLE 3

Determination of Antitumoral Activity of Particles of 4-(N)-squalenoylgemcitabine The cytotoxic activity of SQgem was evaluated on two human tumoral cell lines (KB3-1, cancer of the naso-pharynx and MCF-7, breast cancer) by exposure to SQgem for 72 hours, and compared with the activity of gemcitabine.

The lines were maintained in DMEM medium with 10% foetal calf serum, 2 mM glutamine, 50 mg/l antibiotics, at 37° C., 5% $CO_2$, 95% humidity. The cells were seeded onto a 96 well plate in an amount of $1 \times 10^4$/well; after 24 hours, different dilutions of gemcitabine and SQgem particle were added and incubated for 72 hours. Cellular viability was then determined by the MTT test. The results are expressed as $CI_{50}$, which is the concentration of the molecule at which 50% of the cells are alive.

The results obtained are shown in Table II below. They clearly show that SQgem particles are 5 to 7 times more cytotoxic than the gemcitabine molecule.

TABLE II

| | $CI_{50}$ (μM) after 72 hours | |
|---|---|---|
| | KB3-1 | MCF-7 |
| Gemcitabine | 50.8 ± 49.8 | 29.0 ± 13.9 |
| SQgem | 8.8 ± 4.1 | 4.8 ± 3.9 |

The cytotoxic activity of SQgem at different times was also determined by incubating 100 μM SQgem nanoparticles on two cell lines in the presence and absence of inserts (0.02 μm) (MTT test) (n=3).

Figure 3:
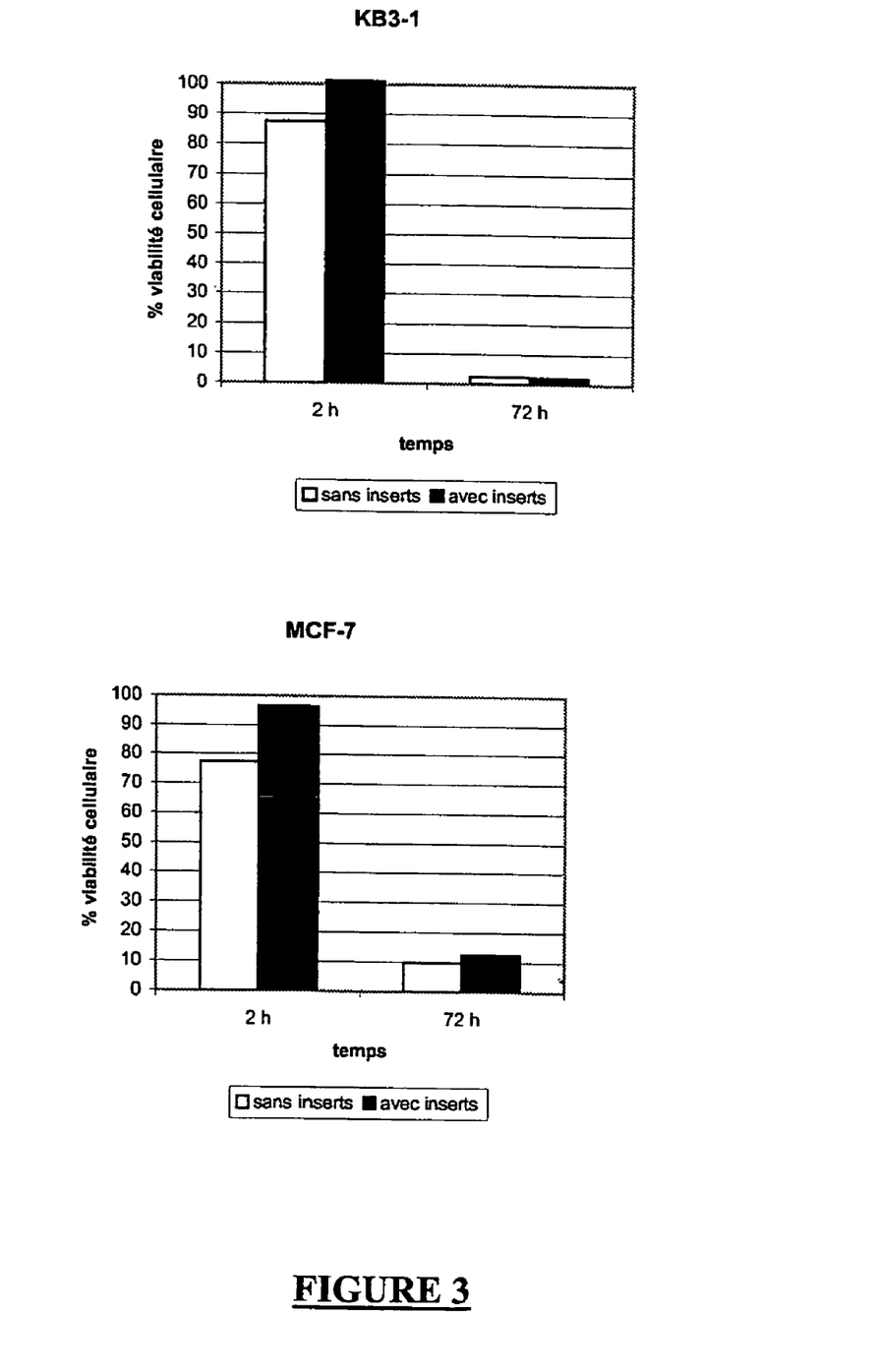
FIG. 3: This shows cell viability as a function of time after incubating 100 μM SQgem nanoparticles on two cell lines in the presence and in the absence of inserts (MTT test) (n=3).

The results obtained are shown in FIG. 3. It should be noted that the anti-cancer activity of SQgem was not reduced with respect to the cytotoxicity tests in the absence of an insert.

EXAMPLE 4

Preparation of PEGylated 4-(N)-squalenoylgemcitabine Nanoparticles 2 mg of 4-(N)-squalenoylgemcitabine and 1.4 mg of cholesterol coupled to polyethylene glycol (Chol-PEG PEGYLATED CHOLESTEROL, SUNBRIGHT CS-020) was dissolved in 1 ml of acetone. This organic phase was added to 2 ml of MilliQ® water with magnetic stirring. After evaporating off the acetone under vacuum, a stable suspension of nanoparticles was obtained. The size of the nanoparticles, determined using the protocol described in example 2, was about 75 nm and the zeta potential was −32.7 mV.

EXAMPLE 5

Preparation of Nanoparticles Constituted by 4-(N)-squalenoylcytarabine (SQara-C)

4-(N)-squalenoylcytarabine was synthesized from squalenic acid by reaction with cytarabine using the procedure described in example 1 for 4-(N)-squalenoylgemcitabine. The particles constituted by SQara-C were obtained by the nano-precipitation technique, as described for the SQgem particles, and their mean hydrodynamic diameter was 110.4±34.1 nm for a concentration of SQara-C in the final suspension of 1 mg/ml (polydispersity index: 0.168).

EXAMPLE 6

Synthesis of Nanoparticles of 5'-squalenoyl-didanosine: 5-(6-oxo-1,6-dihydro-purin-9-yl)-tetrahydro-furan-2-yl-methyl (2S,5R)-((4,8,13,17,21-pentamethyl-docosa-4,8,12,16,20-pentanoate 28 mg of N-hydroxybenzotriazole (0.18 mmol), 36 mg of didanosine (ddI, 0.15 mmol), 70 mg of O-(7-azabenzotriazol-1-yl)-N,N,N',N'-tetramethyluronium hexafluoroborate (0.18 mmol) and finally 62 mg of diisopropylethylamine (0.5 mmol) were added to a solution of 31 mg of (4,8,13,17,21-pentamethyl-docosa-4,8,12,16,20-pentaenoic acid (Sq-COOH, 0.15 mmol) in anhydrous dimethylformamide (1.2 ml). The mixture was stirred for 84 hours at 20° C. in a nitrogen atmosphere, then concentrated under reduced pressure (0.05 Torr). The residue was taken up in 5 ml of a saturated aqueous solution of sodium bicarbonate, and extracted with ethyl acetate (3×10 ml). The organic phase was washed with an aqueous NaCl solution, dried over $MgSO_4$ and concentrated under vacuum. The residue was chromatographed over silica gel ($CH_2Cl_2$/MeOH: 92/8) to produce 37 mg of 5'-squalenoyldidanosine (Yield 58%) in the form of a colorless amorphous solid.

IR ($cm^{-1}$) 3550-2700, 2921, 2856, 1734, 1691, 1590, 1548, 1449, 1380, 1261. $^1$H NMR (200 MHz, $CDCl_3$) δ: 13.0 (s broad, 1H), 8.18 (s, 1H), 8.08 (s, 1H), 6.38 (t, J=4.2 Hz, IH), 5.17-5.00 (m, 5H), 4.40-4.20 (m, 3H), 2.60-1.90 (m, 24H), 1.67 (s, 3H), 1.60 (s broad, 15H). $^{13}$C NMR (50 MHz, $CDCl_3$) δ: 173.27 ($CO_2$), 159.20 (CO), 148.34 (C), 144.3 (CH) 138.60 (CH), 135.23 (C), 135.03 (C), 135.00 (C), 133.09 (C), 131.31 (C), 125.56 (CH), 125.38 (C), 125.54 (CH), 124.53 (CH), 124.40 (2 CH), 85.94 (CH), 79.60 (CH), 65.07 ($CH_2$), 39.86 ($CH_2$), 39.83 ($CH_2$), 39.68 ($CH_2$), 34.67 ($CH_2$), 33.12 ($CH_2$), 33.01 ($CH_2$), 28.39 ($CH_2$), 28.38 ($CH_2$), 29.9 ($CH_2$), 26.83 ($CH_2$), 26.79 ($CH_2$), 26.28 ($CH_2$), 25.77 ($CH_3$), 17.77 ($CH_3$), 16.51 (2 $CH_3$), 16.10 ($CH_3$), 16.00 ($CH_3$).

The same compound could be obtained in a yield of 10% using EDCI as the coupling agent, while condensation between the squaloyl acid chloride and dI produced it in a yield of 15%.

The particle size was determined using the protocol described in example 2. The hydrodynamic diameter mean was 152 nm, measured with a standard deviation of 34.4 nm and a polydispersity index of 0.1.

EXAMPLE 7

Synthesis of Nanoparticles of 5'-squalenoyl-zidovudine: 3-azido-5-(5-methyl-2,4-dioxo-3,4-dihydro-2H-pyrimidin-1-yl)-tetrahydro-furan-2-yl-methyl (2S,3S,5R)-4,8,13,17,21-pentamethyl-docosa-4,8,12, 16,20-pentaneoate 45 mg of N-hydroxybenzotriazole (0.29 mmol), 79 mg of zidovudine (AZT, 0.24 mmol), 113 mg of O-(7-azabenzotriazol-1-yl)-N,N,N',N'-tetramethyluronium hexafluoroborate (0.29 mmol) and finally 102 mg of diisopropylethylamine (0.5 mmol) were added to a solution of 50 mg of (4,8,13,17, 21-pentamethyl-docosa-4,8,12,16,20-pentaenoic acid (Sq-COOH, 0.15 mmol) in anhydrous dimethylformamide (2 ml). The mixture was stirred for 90 hours at 20° C. in a nitrogen atmosphere, then concentrated under reduced pressure (0.05 Torr). The residue was taken up in 10 ml of a saturated aqueous solution of sodium bicarbonate, and extracted with ethyl acetate (3×15 ml). The organic phase was washed with an aqueous NaCl solution, dried over $MgSO_4$ and concentrated under vacuum. The residue was chromatographed over silica gel ($CH_2Cl_2$/MeOH: 97/3) to produce 52 mg of 5'-squalenoyl zidovudine (yield 43%) in the form of a colorless amorphous solid.

IR ($cm^{-1}$) 3158, 2920, 2854, 2105, 1741, 1690, 1449, 1381, 1270. $^1$H NMR (200 MHz, $CDCl_3$) δ: 8.2 (s broad, 1H), 7.22 (s, 1H), 6.12 (t, J=6.4 Hz, 1H), 5.17-5.00 (m, 5H), 4.40 (dd, J=12.2 Hz, 4.6 Hz, 1H), 4.30 (dd, 12.2 Hz, 3.8 Hz, 1H), 4.10-4.05 (m, 1H), 2.55-2.20 (m, 5H), 2.10-1.90 (m, 18H), 1.94 (s, 3H), 1.69 (s, 3H), 1.60 (s broad, 15H). $^{13}$C NMR (50 MHz, CDCl$_3$) δ: 172.87 (CO$_2$), 163.57 (CO), 150.12 (CO), 135.31 (C), 135.27 (CH), 135.04 (C), 134.91 (C), 132.86 (C), 131.35 (C), 125.79 (CH), 124.67 (CH), 124.56 (CH), 124.40 (CH), 124.37 (CH), 111.43 (C), 85.64 (CH), 82.00 (CH), 63.36 (CH$_2$), 60.81 (CH), 39.88 (CH$_2$), 39.85 (CH$_2$), 39.68 (CH$_2$), 37.75 (CH$_2$), 34.62 (CH$_2$), 33.18 (CH$_2$), 29.81 (CH$_2$), 28.41 (CH$_2$), 28.39 (CH$_2$), 26.91 (CH$_2$), 26.82 (CH$_2$), 26.81 (CH$_2$), 25.80 (CH$_3$), 17.79 (CH$_3$), 16.17 (2CH$_3$), 16.16 (CH$_3$), 16.12 (CH$_3$), 16.05 (CH$_3$), 12.73 (CH$_3$).

The particle size was determined using the protocol described in example 2. The hydrodynamic diameter mean was 150-170 nm.

EXAMPLE 8

Preparation of Nanoparticles Constituted by 4-(N)-squalenoyl Acyclovir (SQACV)

The 4-(N)-squalenoyl acyclovir was synthesized from squalenic acid by reaction with acyclovir. In the procedure used, it was possible to obtain either an ester linkage or an amide linkage between the squalene chain and the acyclovir. Particles constituted by SQACV were obtained using the nano-precipitation technique as described for particles of SQgem, and their mean hydrodynamic diameter was 217.5+ 37.9 nm for a concentration of SQACV in the final suspension of 1 mg/ml (Polydispersity index: 0.038).

The invention claimed is:

1. A 2',2'-difluoro-2'-deoxycytidine derivative with general formula (I)

in which:
R$_1$, R$_2$ and R$_3$, which may be identical or different, independently of each other represent a hydrogen atom or an at least C$_{18}$ hydrocarbon acyl radical which is acyclic, non-linear and unsaturated with a conformation such that it is capable of endowing said compound with general formula (I) with a compacted form, in a polar solvent medium;
at least one of groups R$_1$, R$_2$ and R$_3$ being other than a hydrogen atom.

2. The 2',2'-difluoro-2'-deoxycytidine derivative of claim 1, characterized in that said radical is a squalenoyl radical or a derivative thereof.

3. The 2',2'-difluoro-2'-deoxycytidine derivative of claim 1, characterized in that it comprises a hydrocarbon acyl derivative as the radical R$_1$.

4. The 2',2'-difluoro-2'-deoxycytidine derivative of claim 1, with the general formula (IA)

in which R$_2$ and R$_3$ are as defined in claim 1 and R'$_1$ represents a squalenoyl radical or a derivative thereof.

5. The derivative according to claim 4, wherein R$_2$ and R$_3$ each represent a hydrogen atom.

6. Nanoparticles of a 2',2'-difluoro-2'-deoxycytidine derivative with general formula (I):

in which:
R$_1$, R$_2$ and R$_3$, which may be identical or different, independently of each other represent a hydrogen atom or an at least C$_{18}$ hydrocarbon acyl radical which is acyclic, non-linear and unsaturated with a conformation such that it is capable of endowing said compound with general formula (I) with a compacted form, in a polar solvent medium;
at least one of groups R$_1$, R$_2$ and R$_3$ being other than a hydrogen atom.

7. Nanoparticles of 4-(N)-squalenoylgemcitabine.

8. The nanoparticles according to claim 6, wherein said nanoparticles have a mass average size is 30 nm to 500 nm.

9. The nanoparticles according to claim 7, wherein said nanoparticles have a mass average size is 30 nm to 500 nm.

10. The nanoparticles according to claim 6, wherein said nanoparticles are associated with at least one lipophilic derivative of polyethylene glycol.

11. The nanoparticles according to claim 7, wherein said nanoparticles are associated with at least one lipophilic derivative of polyethylene glycol.

12. The nanoparticles according to claim 10, wherein said lipophilic derivative of polyethylene glycol is polyethylene glycol cholesterol.

13. A process for preparing nanoparticles of a 2',2'-difluoro-2'-deoxycytidine derivative with general formula (I):

in which $R_1$, $R_2$ and $R_3$, which may be identical or different, independently of each other represent a hydrogen atom or an at least $C_{18}$ hydrocarbon acyl radical which is acyclic, non-linear and unsaturated with a conformation such that it is capable of endowing said compound with general formula (I) with a compacted form, in a polar solvent medium; at least one of groups $R_1$, $R_2$ and $R_3$ being other than a hydrogen atom, comprising at least the following steps of dissolving at least one 2',2'-difluoro-2'-deoxycytidine derivative with general formula (I)

in which $R_1$, $R_2$ and $R_3$, which may be identical or different, independently of each other represent a hydrogen atom or an at least $C_{18}$ hydrocarbon acyl radical which is acyclic, non-linear and unsaturated with a conformation such that it is capable of endowing said compound with general formula (I) with a compacted form, in a polar solvent medium; at least one of groups $R_1$, $R_2$ and $R_3$ being other than a hydrogen atom in at least one organic solvent in a concentration which is sufficient to obtain, when adding the resulting mixture to an aqueous phase, with stirring, the instantaneous formation of nanoparticles in suspension in said aqueous phase and, if appropriate, isolating said nanoparticles.

14. The process according to claim 13, wherein it is carried out in the absence of a surfactant.

15. The process according to claim 13, wherein it is carried out in the presence of a lipophilic derivative of polyethylene glycol.

16. The process according to claim 15, wherein said lipophilic derivative of polyethylene glycol is polyethylene glycol cholesterol.

17. A pharmaceutical composition comprising, as an active material, at least one 2',2'-difluoro-2'-deoxycytidine derivative with general formula (I)

in which $R_1$, $R_2$ and $R_3$, which may be identical or different, independently of each other represent a hydrogen atom or an at least $C_{18}$ hydrocarbon acyl radical which is acyclic, non-linear and unsaturated with a conformation such that it is capable of endowing said compound with general formula (I) with a compacted form, in a polar solvent medium; at least one of groups $R_1$, $R_2$ and $R_3$ being other than a hydrogen atom or nanoparticles thereof, in association with at least one pharmaceutically acceptable vehicle.

18. The nanoparticles according to claim 6, as anti-cancer agents.

19. The nanoparticles according to claim 6, as antiviral agents.

* * * * *